United States Patent [19]
Petzoldt et al.

[11] Patent Number: 5,102,793
[45] Date of Patent: Apr. 7, 1992

[54] STEREOSPECIFIC KETO REDUCTION OF BICYCLOOCTANDIONE-CARBOXYLIC ACID ESTERS BY MICROORGANISMS

[75] Inventors: Karl Petzoldt; Helmut Dahl; Helmut Vorbruggen, all of Berlin, Fed. Rep. of Germany

[73] Assignee: Schering Aktiengesellschaft, Berlin, Fed. Rep. of Germany

[21] Appl. No.: 237,110

[22] PCT Filed: Nov. 12, 1987

[86] PCT No.: PCT/DE87/00517
§ 371 Date: Jul. 13, 1988
§ 102(e) Date: Jul. 13, 1988

[87] PCT Pub. No.: WO88/03568
PCT Pub. Date: May 19, 1988

[30] Foreign Application Priority Data
Nov. 13, 1986 [DE] Fed. Rep. of Germany ....... 3638759

[51] Int. Cl.$^5$ .................. C12P 17/08; C12P 17/02; C12N 1/14; C12N 1/16

[52] U.S. Cl. .................. 435/124; 435/123; 435/280; 435/939; 435/911; 435/254; 435/255

[58] Field of Search ............... 435/123, 124, 921, 939, 435/911, 254, 255, 280

[56] References Cited
U.S. PATENT DOCUMENTS
4,004,978  1/1977  McMullen .............................. 35/923

OTHER PUBLICATIONS
Mori et al., *Tetrahedon*, vol. 42, No. 1, pp. 435–444 1986.
ATCC Catalogue of fungi; 1987, pp. 316–317.
Kieslich, K., *Microbial Transformations*, 1976, Wiley & Sons, pp. 639–640
Rose A., "The Yeasts", vol. 1, 1987, pp. 30–38.

*Primary Examiner*—Douglas W. Robinson
*Assistant Examiner*—Irene Marx
*Attorney, Agent, or Firm*—Millen, White & Zelano

[57] ABSTRACT

A microbiological process for sterospecific monoketo reduction of racemic 3-keto-bicyclic carbacyclin intermediates to the corresponding optically active 30α hydroxy compounds is provided.

3 Claims, No Drawings

STEREOSPECIFIC KETO REDUCTION OF BICYCLOOCTANDIONE-CARBOXYLIC ACID ESTERS BY MICROORGANISMS

The invention relates to a microbiological process for stereospecific mono-keto reduction of racemic bicyclic carbacyclin intermediate stages of the formula (±)-II to the corresponding optically active 3alpha-hydroxy compounds of the formula (+)-I.

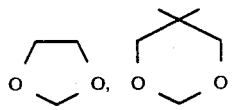

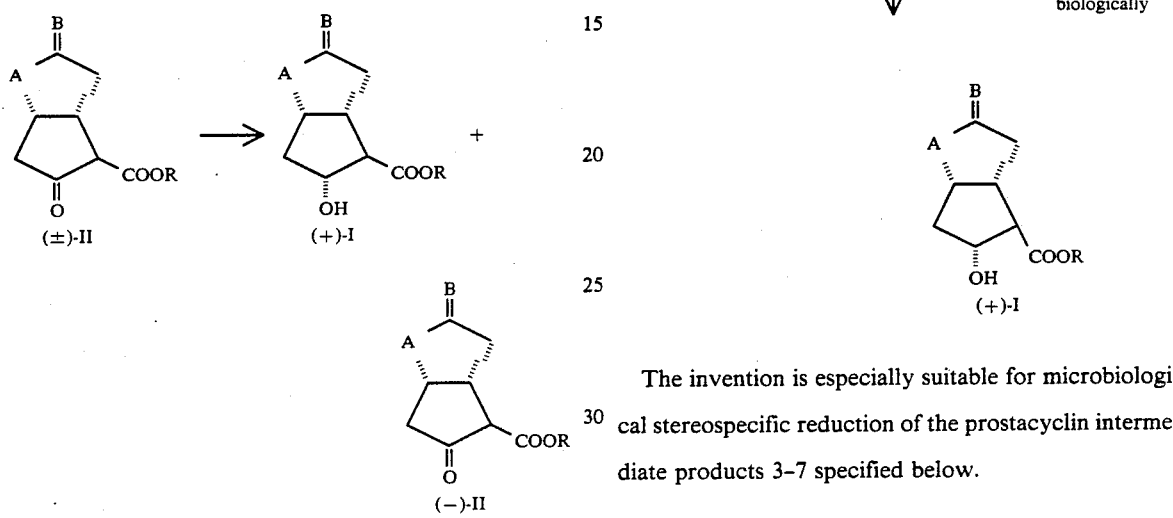

The radicals A, B and R in the formula mean:
A: $CH_2$ or CH—COOR,
B: oxygen

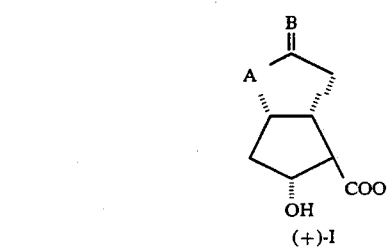

or other ketal radicals and
R: $C_1$-$C_6$ alkyl.

The process is characterized in that a ketone of the general formula (±)-II, in which A, B and R have the meaning indicated above, is treated with microorganisms, and the resulting 3alpha-hydroxy-prostacyclin intermediate product, which in its configuration corresponds to the natural $PGI_2$, is isolated.

In a second embodiment of the stereospecific keto reduction process according to the invention not the enantiomers of the racemic synthon (±)-II correspondingly configured to the natural $PGI_2$ but the antipodal form is reduced by microorganisms. In this case, the naturally configured keto enantiomers (+)-II, which has remained unchanged in the microbiological transformation, is used for the synthesis of prostacyclins, by reducing it either chemically (for example, with sodium boron hydride) or microbiologically to (+)-I.

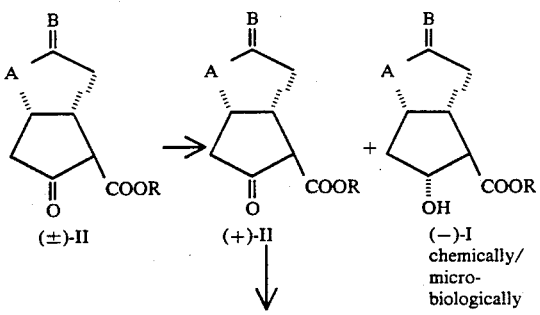

The invention is especially suitable for microbiological stereospecific reduction of the prostacyclin intermediate products 3-7 specified below.

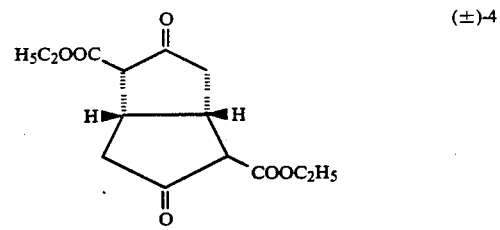

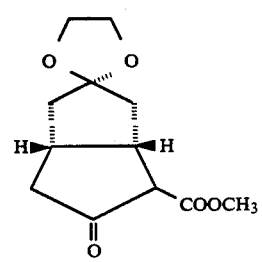

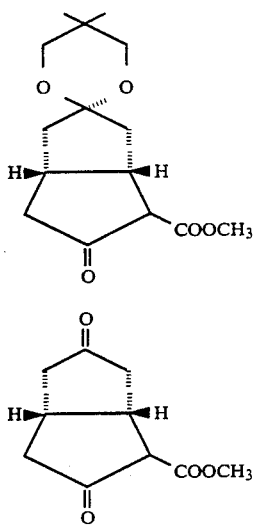

(±)-6

(±)-7

Optically active 6alpha-carbaprostacyclin and especially some compounds derived for it have, as stable analogs of the natural prostacyclin (PGI₂), a high therapeutic use [R. C. Nickolson, M. H. Town, H. Vorbrueggen: Prostacyclin Analogs, Medical Research Reviews, Vol. 5, No. 1, pp. 1-53 (1985). The syntheses specified in this more recent survey are long and lead partially only to racemic carbacyclins. The syntheses, which lead to the carbacyclins in the absolute configuration corresponding to the natural PGI₂, are especially costly. This is due to the fact that readily accessible, suitable initial materials are achiral and the optical activity must be introduced into the intermediate stages suitable for this purpose only in the course of the synthesis.

Several syntheses already start from optically active 7alpha-hydroxy-6beta-hydroxymethyl-2-oxa-bicyclo[3.3.0]octan-3-one derivatives. Thus the problem of the introduction of optical activity is indeed solved. But further multistage synthesis sequences must still be performed for the substitution of the 2-oxa function by a methylene group, to reach derivatives of 3alpha-hydroxy-2beta-hydroxymethyl-bicyclo[3.3.0]octan-7-one, which are suitable only for the attachment of alpha and omega chains typical, respectively, for the carbacyclin analogs.

A more recent publication describes the use of cis-bicyclo[3.3.0]octan-3,7-dione derivatives for synthesis of optically active carbacyclins. Kojima et al. describe in Chem. Pharm. Bull. 33, 2688 (1985) a process, which includes the separation of diastereomeric salts of the racemic 7,7-ethylenedioxy-3alpha-hydroxy-cis-bicyclo[3.3.0]octane-2-carboxylic acid.

This process also still requires 7 reaction steps to reach the starting material for carbacyclin analogs starting from 3-oxaglutaric esters. In addition, an unstable beta keto acid intermediate stage is passed through.

Further, for the production of optically active carbacyclin analogs, as described above, no synthesis method, which allows a simple production, is known.

The microbiological reduction according to the invention of the prostacyclin intermediate products specified above is performed with the following microorganism strains or enzymes isolated from them:

*Rhizopus oryzae* (CBS 32947)
*Rhizopus arrhizus* (ATCC 34102)
*Rhizopus arrhizus* (ATCC 10260)
Rhodotorula spec. (ATCC 18101)
*Rhodotorula mucilaginosa* (NCYC 63)
*Rhodotorula glutinis* (ATCC 2527)
*Candida solani* (IFO 968)
Rhizopus stolonifer (ATCC 6227 b)

Among the different types of classes of microorganisms indicated, naturally differences of the effectiveness in the keto reduction according to the invention occur.

On 11/11/1986 the strains *Rhizopus oryzae* (DSM 3899) and *Rhizopus arrhizus* (DSM 3898) were deposited with the German Collection of Microorganism, Mascheroder Weg 1b,1)-3300 Braunschweig, West Germany.

Pharmacologically effective prostacyclins can be produced from the optically active 3alpha-hydroxy compounds of general formula (+)-I produced by the process according to the invention. For example, starting from (+)-I it is possible to arrive at the active ingredient Iloprost (described in EP 11591).

Thus the invention relates to a process for the production of 3alpha-hydroxy prostacyclin intermediate products of the general formula (+)-I

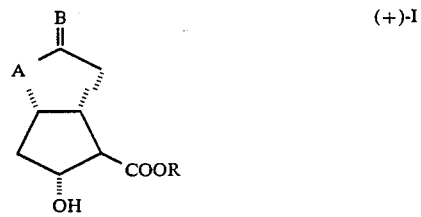

(+)-I in which
A is the radicals —CH₂— or >CH—COOR,
B is oxygen or the double-bond radical —O—X—O— with X as straight-chain or branched-chain alkylene with 1-7 carbon atoms and
R is a straight-chain or branched-chain alkyl group with 1-6 carbon atoms or benzyl,
characterized in that a racemic bicyclooctanedione of the formula (±)-II

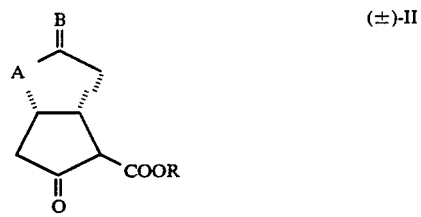

(±)-II in which A, B and R have the meaning indicated above, is treated with Rhizopus, Rhodotorula or Candida strains, and for the case that the strain used reduces the (−) form from the racemate (±)-II, a chemical or microbiological reduction of the unchanged bicyclooctanedione of formula (+)-II follows.

If X is a straight-chain or branched-chain alkylene radical with 1-7C atoms, the following radicals are meant: —(CH₂)ₙ— with n=1-7 (methylene, ethylene, tri-, tetra-, penta-, hexa- and hepta-methylene), —C(CH₃)₂, —CH(CH₃)—, —CH(CH₃)—CH2—, —C(CH₃)₂-CH₂, —CH₂—CH(CH₃)—, CH₂—C(CH₃-)₂—, —CH₂—CH(CH₃)-CH₂, —CH₂—C(CH₃)₂—CH₂—, —CH(C₂H₅)—, C(C₂H₅)₂, —CH(C₂H₅)—CH₂—, —C(C₂H₅)₂—CH₂—, —CH- $_2$—CH(C$_2$H$_5$)—, —CH$_2$—C(C$_2$H$_5$)$_2$, —CH$_2$—CH(C$_2$H$_5$)—CH$_2$, —CH$_2$—C(C$_2$H$_5$)$_2$— etc.

By R as C$_1$–C$_6$ is understood methyl, ethyl, n-propyl, isopropyl, n-butyl, isobutyl, sec-butyl, tert-butyl, n-pentyl, isopentyl, sec-pentyl, neopentyl, n-hexyl isohexyl etc Depending on the meaning of B ultimately desired, the protecting groups can be split off by method known in the art.

First, submerged cultures are cultured under culture conditions usually used for said microorganisms in a suitable nutrient medium and under aeration. Then to the cultures are added the substrate (dissolved in a suitable solvent or preferably in emulsified form) and fermented, until a maximum substrate change is achieved.

Suitable substance solvents are, for example, methanol, ethanol, glycol monomethyl ester, dimethylformamide or dimethyl sulfoxide. The emulsification of the substrate can be caused, for example, by spraying the substrate in micronized form or dissolved in a water-miscible solvent (such as methanol, ethanol, acetone, glycol monomethyl ether, dimethylformamide, dimethyl sulfoxide) under vigorous turbulence into (preferably decalcified) water, which contains the usual emulsion auxiliary agents. Suitable emulsion auxiliary agents are nonionogenic emulsifiers such as, for example, ethylene oxide feedstock of fatty acid esters of polyglycols. There can be mentioned, for example, as suitable emulsifiers the commercial wetting agents Tegin ®, Tagat ® and Span ®.

Emulsification of the substrates often makes possible an increased throughput and thus an increase of substrate concentration. But is obviously possible in the process according to the invention to use other methods for increasing the substrate throughput, as is well known to a fermentation expert.

The optimal substance concentration, the substrate addition time and fermentation period depend on the structure of the substrate used and the type of microorganism used. These amounts must be determined as is generally necessary in microbiological reactions, in particular cases by preliminary tests as are familiar to the man of the art.

Production of the initial compounds cis-Bicyclo[3.3.0]octan,3,7-dione-2,6-dicarboxylic acid ester Dimethyl ester 3 is known in the literature [Weiss et al., J. Org. Chem. 42, 3089 (1977)] and starting from 3-oxaglutaric acid dimethyl ester is readily accessible in two reaction steps by cis-bicyclo[3.3.0]octan-3,7-dione,2,4,6,8-tetracarboxylic acid tetramethyl ester.

Diethyl ester 4 can be produced from cis-bicyclo[3.3.0]octane-3,7-dione-2,4,6,8-tetracarboxylic acid tetraethyl ester (EP 33863).

A higher ester can be produced analogously to this process or by transesterification of dimethyl ester according to the method of D. F. Faber et al [J. Org. Chem. 50, 3618 (1985).

7,7-Ethylenedioxy-cis-bicyclo[3.3.0]octan-3-one-2-carboxylic acid methyl ester (5)

Production is described by various authors (cf. l.c. Review of Nickolson et al).

7,7-(2,2-Dimethyltrimethylenedioxyl)-cis-bicyclo[3.3.0]octan-3-one-2-carboxylic acid methyl ester (6)

Production takes place according to the above-named literature process from 3,3-(2,2-dimethyltrimethylenedioxy)-cis-bicyclo[3.3.0]octan-7-one [E. Carceller et al. Tetrahedron Letters 25, 2019 (1984)].

cis-Bicyclo[3.3.0]octan-3,7-dione-2-carboxylic acid methyl ester (7)

The compound can be produced, for example, by ketal cleavage of 5 or 6 with acids and water or also by carboxylation and esterification of cis-bicyclo[3.3.0]octan-3,7-dione, for example, with magnesium methyl carbonate [Reagent Production: M. Stiles, H. L. Finkbeiner, J. Amer. Chem. Soc. 85, 616 (1963)].

The (1S,5S,6R,7R)-7-hydroxy-bicyclo[3.3.0]octan-3-one-2,6-dicarboxylic acid diester obtained by microbiological reduction can be reacted into carbacyclin according to usual chemical processes, for example, to (1S,2R,3R,5R)-3-hydroxy-7,7-ethylenedioxy-bicyclo[3.3.0]octan-3-one-2-carboxylic acid methyl ester, whose reaction into optically active carbacyclin was described in the meantime by Kojima et al. Of course, the intermediate products produced according to the process of the invention can also produce carbacyclin analogs with modified structures in the alpha and/or beta chain.

The over-abundant carbon ester group is decarbalkoxylated as beta-keto ester according to processes known in the art. Especially suitable for this purpose are reactions with 1,4-diazabicyclo[2.2.2]octane [e.g., according to Miles et al., J.Org.Chem. 39, 2647 (1974) or with halide ions in dimethyl sulfoxide or dimethylformamide [Krapcho, Synthesis 1982, 805, or McMurry, Org. Reactions 24, 187 (1976). Thus (1S,2R,3R,5R)-3-hydroxy-bicyclo[3.3.0]octan-7-one-2-carboxylic acid ester is obtained.

The (1S,2R,3R,5R)-3-hydroxy-bicyclo[3.3.0]octan-7-one-2-carboxylic acid esters can be reacted into the ketals by the usual processes, by reacting them with 1,2- or 1,3-diols under catalysis with acid or acid salts and removal of the reaction water by azeotropic distillation or water absorbing agents. With the use of ethylene glycol the starting material for carbacyclin described by Kojima is obtained.

EXAMPLE 1 cis-Bicyclo[3.3.0]octan-3,7-dione-,2,6-dicarboxylic acid diethyl ester 25 g of cis-bicyclo[3.3.0]octan-3,7-dione-2,4,6,8-tetracarboxylic acid tetraethyl ester is added to a solution of 14.1 g of sodium hydroxide in 68.5 ml of ethanol and 175 ml of dimethyl sulfoxide, heated to 50° C. and stirred for 18 hours at this temperature under nitrogen. After cooling, it is poured onto 750 ml ice water, acidified to pH 5–6 with acetic acid, extracted with ethyl acetate, washed with sodium hydrogen carbonate solution, dried with sodium sulfate and concentrated in a vacuum. After recrystallization from ethanol, 13.37 g of product with a melting point of 98°–100° C. is obtained.

EXAMPLE 2

7,7-(2,2-dimethyl-trimethylenedioxy)-cis-bicyclo[3.3.0]octan-3-one-2-carboxylic acid methyl ester 38.34 g of 55–60% sodium hydride is suspended in 616 ml of dimethyl carbonate, heated under nitrogen to 50° C. and a small amount of the solution of 49.31 g of 3,3-(2,2-dimethyltrimethylenedioxy)-cis-bicyclo[3.3.0]octan-7-one in 370 ml of dimethyl carbonate is added thereto. The reaction is induced by addition of 2 ml of methanol, the remaining solution is added thereto and stirring takes place a total of 7.5 hours at 50° C. It is cooled in an ice bath, the excess sodium hydride is decomposed with methanol, water is added, and it is neutralized with acetic acid. The product is extracted with dichloromethane, concentrated in a vacuum and the product is crystallized with hexane. 53.44 g of the product with a melting point of 72° C. is obtained.

EXAMPLE 3 cis-Bicyclo[3.3.0]octan-3,7-dione-2-carboxylic acid methyl ester a) 15 g is added of 7,7-(2,2-dimethyltrimethylenedioxy)-cis-bicyclo[3.3.0]octan-3-one-2-carboxylic acid methyl ester in 350 ml of acetone, 7.23 g of potassium hydrogen sulfate is added and heated for 1 hour to 40° C. After cooling it is neutralized with 1 n potassium hydroxide solution, the acetone is distilled off in a vacuum and it is extracted with dichloromethane. 10.6 g of product, which can be recrystallized from diisopropyl ether (melting point 69° C.) is obtained.

b) 26.0 g of cis-bicyclo[3.3.0]octan-3,7-dione with 350 ml of 2.15-molar magnesium methyl carbonate solution in dimethylformamide is heated under nitrogen for 4 hours, it is cooled and the mixture is slowly added into 500 ml of 8.8-molar methanolic hydrochloric acid cooled to −65° to −50° C. It is allowed to heat overnight to 20° C., is concentrated in a vacuum, mixed with water and extracted with diethyl ether. After drying with sodium sulfate it is concentrated in a vacuum and the resulting residue is chromatographed on silica gel with ethyl acetate/methanol 95:5. 21.31 g of product is obtained.

(Melting point 67°–69° C.).

EXAMPLE 4

A 4–8 day old of slant agar culture of the strain *Rhizopus oryzae* (CBS 32 947) is rinsed with 3 ml of physiological sodium chloride solution and a 2-liter Erlenmeyer flask is inoculated with it, which contains 500 ml of sterile nutrient solution of the following composition:

3.0% glucose
1.0% corn steep liquor
0.2% $NaNO_3$
0.1% $KH_2PO_4$
0.2% $K_2HPO_4$
0.05 % $MgSO_4.7H_2O$
0.002% $FeSO_4.7H_2O$
0.05% KCl The culture is shaken for 56 hours in a rotary shaker at 30° C., and it grows mostly into large clumps. For better inoculability the clumps are reduced to small pieces in a inoculation flask in a way gentle to the cells under sterile conditions with an Ultra-Turrax T 45.

A 40-liter steel fermenter, which is filled with 28 liters of sterilized nutrient solution of the same composition as the preliminary culture, is inoculated with the turraxed fungus suspension of two inoculation flasks. At the same time the substrate suspension (400 mg/l) is added.

Substance suspension: 12 g of (±)-cis-3,7-dioxobicyclo[3.3.0]octan-2,6-dicarboxylic acid dimethyl ester is homogenized in 1200 ml of autoclaved 2% Tween 80 solution (deionized water) in the substrate flask with an Ultra-Turrax T45.

After a contact time of 52 hours about 50% of the racemic ketone used is reacted. The culture broth is now suctioned off over a cellulose gauze, the filtrate is extracted once with half and then twice more with ⅓ each of the culture volume with MIBK. The extracts are combined and concentrated by evaporation, and the fumaric acid (1–1.5 g/l), formed during fermentation, is crystallized out. After filtering off of the fumaric acid, the filtrate is concentrated to dryness and the residue is chromatographed over a silica gel column by means of solvent gradient hexane-ethyl acetate for separation of the unreacted ketone as well as purification of the 3alpha-OH compound. 4.9 g of (+)-cis-3alpha-hydroxy-7-oxo-bicyclo[3.3.0]octan-2,6-dicarboxylic acid dimethyl ester is obtained of a melting point of 54°–56° C. with an amount of rotation $[alpha]^D +51°$ (c=1, chloroform), which corresponds to an enantiomer purity of over 90%.

EXAMPLE 5

A slant agar culture of the strain Rhodotorula spec. ATCC 18101 is rinsed with 3 ml of physiological sodium chloride solution and thus a 2-liter Erlenmeyer flask is inoculated with it, which contains 500 ml of sterile nutrient solution of the following composition:

5% dextrose monohydrate
2% corn steep liquor
pH 6.5.

After 2-day shaking in a rotary shaker at 30° C. a 5-liter fermenter, which is filled with 3.5 liters of sterilized nutrient solution of the same composition as the preliminary culture, is inoculated with 250 ml of this preliminary culture. The culture is germinated for 12 hours under aeration (3.75 l/min) and stirring (220 rpm) with the pH kept constant at 6.5 and then the substrate in the form of a sterile filtered solution of 1.5 g of (±)-7,7-(2,2-dimethyltrimethylenedioxy)-cis-bicyclo[3.3.0]octan-3-one-2-carboxylic acid methyl ester in 50 ml of ethanol is added. After a contact time of 12 hours 50% of the racemic ketone used is reacted. The culture broth is now extracted once with half and then twice more with ⅓ each of the culture volume with methyl isobutyl ketone. The extracts are combined and evaporated to dryness in a vacuum. The remaining residue is chromatographed over a silica gel column (solvent gradient dichloromethane-dichloromethane/8% acetone) for separation of the reduced (−) enantiomers. Fraction I contains the naturally configured unreacted (+) ketone enantiomer. After concentration to dryness and crystallization from hexane, 580 mg of (+)-7,7-(2,2-dimethyltrimethylenedioxy)-cis-bicyclo[3.3.0]octan-3-one-2carboxylic acid methyl ester of a melting point of 64°–65° C. is obtained.

For chemical reduction, 500 mg of (+)-7,7-(2,2-dimethyltrimethylenedioxy)-cis-bicyclo[3.3.0]octan-3-one 2-carboxylic acid methyl ester is dissolved in 10 ml of methanol and refluxed for 1 hour. Then it is cooled to −40° C., 200 mg of $NaBH_4$ is added and it is stirred at this temperature for 1 hour. Then 2 ml of acetone is added, it is stirred for 30 minutes more, adjusted to pH 7 with dilute acetic acid, diluted with water and extracted with dichloromethane. The extract is concentrated to dryness, the residue is dissolved in 10 ml of methanol, 100 mg of sodium methylate is added and stirring is performed for 4 hours at 40° C. The solution is brought to pH 5.5 with 2n $H_2SO_4$ with ice cooling, the methanol is distilled off, the residue is taken up in water and extracted 3 times with dichloromethane. The extract is washed neutral, dried over $Na_2SO_4$ and concentrated to dryness. After crystallization from hexane, 420 mg of (+)-7,7-(2,2-dimethyltrimethylenedioxy)-3alpha-hydroxy-cis-bicyclo[3.3.0]octan-2-carboxylic acid methyl ester of a melting point of 59°-61° C. and an amount of rotation of [alpha]$_D$+25.1° (c=1.2, chloroform) is obtained.

EXAMPLE 6

(1S,2R,3R,5R)-3-hydroxy-cis-bicyclo[3.3.0]octan-7-one-2-carboxylic acid methyl ester 3.41 g of the product obtained in example 4 is heated for 1 hour under nitrogen with 0.35 g of sodium chloride and 41.2 ml of dimethylformamide, which contains 3% water. It is distilled off to a great extent in a vacuum and 3.32 g of the raw product is obtained, which in used in the next stage.

The purified product shows a melting point of 55° C. and a specific amount of rotation (c=1 in chloroform) of [alpha]$_D$ +6.0°.

EXAMPLE 7

(1S,2R,3R,5R)-7,7-ethylenedioxy-3-hydroxy-cis-bicyclo[3.3.0]octan-2-carboxylic acid methyl ester The raw product from example 6 is refluxed in 50 ml of benzene with 1.13 g of ethylene glycol and 0.35 g of 4-toluenesulfonic acid for 3 hours and the resulting water is separated. After cooling, it is mixed with 0.5 g of sodium hydrogen carbonate, extracted with water and concentrated in a vacuum. It is chromatographed on silica gel with hexane-ethyl acetate mixtures, and 2.50 g of the product is obtained as colorless oil.

Specific amount of rotation (c=1 in chloroform) [alpha]$_D$ +26.5°.

What is claimed is:

1. A process for the production of a 3α-hydroxy prostacyclin intermediate product of the formula (+)-I

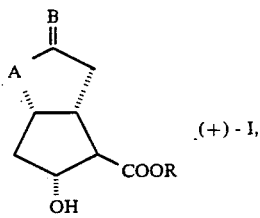

wherein
A is the radical >CH—COOR,
B is oxygen and
R is methyl,
comprising treating a racemic bicyclooctanedione of formula (±)-II

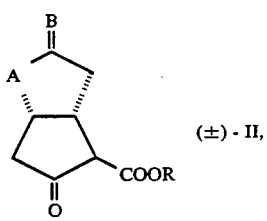

wherein A, B and R have the above-indicated meanings, with a culture of *Rhizopus oryzae* CBS 32 947 to stereospecifically produce a compound of the formula (+)-I while essentially not altering the compound of the formula (−)-II, and separating the thus-obtained compounds.

2. A process for the production of a 3α-hydroxy prostacyclin intermediate product of the formula (+)-I

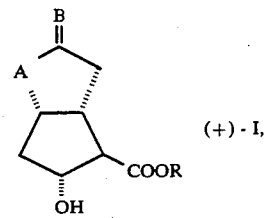

wherein
A is the radical —CH$_2$—,
B is the double-bond radical —O—X—O— wherein X is

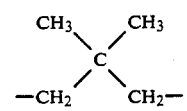

and
R is methyl,
comprising treating a racemic bicyclooctanedione of formula (±)-II

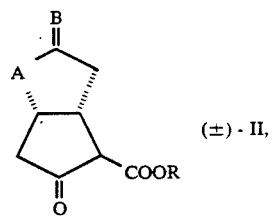

wherein A, B and R have the above-indicated meanings, with a culture of Rhodotorula spec. ATCC 18101 to stereospecifically produce a compound of the formula (−)-I while essentially not altering the compound of the formula (+)-II, and further chemically reducing the unchanged bicyclooctanedione of formula (+)-II after separation from the compound of formula (−)-I.

3. A process for stereospecifically producing a compound of formula (−)-I

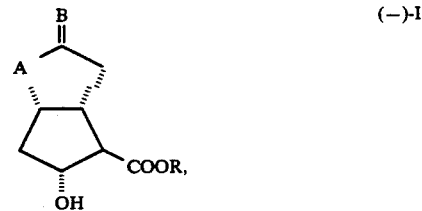

wherein
A is the radical —CH$_2$—,
B is the double-bond radical —O—X— wherein X is

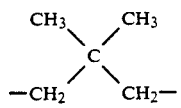
and
R is methyl, comprising treating a racemic bicyclooctanedione of formula (±)-II
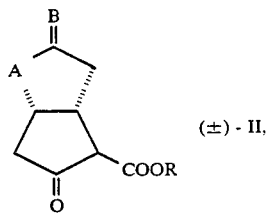
wherein A, B and R have the above-indicated meanings, with a culture of Rhodotorula spec. ATCC 18101 to stereospecifically produce a compound of the formula (−)-I while essentially not altering the compound of the formula (+)-II, and separating the thus-obtained compounds.
* * * * *